United States Patent [19]

Birum et al.

[11] 4,179,482
[45] Dec. 18, 1979

[54] 2-CHLOROETHYL PHOSPHONATE COMPOSITIONS

[75] Inventors: Gail H. Birum, Kirkwood; Richard F. Jansen, St. Louis, both of Mo.

[73] Assignee: Monsanto Company, St. Louis, Mo.

[21] Appl. No.: 945,668

[22] Filed: Sep. 25, 1978

Related U.S. Application Data

[63] Continuation-in-part of Ser. No. 855,533, Nov. 28, 1977, abandoned, which is a continuation of Ser. No. 831,707, Sep. 9, 1977, abandoned.

[51] Int. Cl.$^2$ ............................. C07F 9/40; C08J 9/00
[52] U.S. Cl. ..................................... 260/941; 260/969; 521/108
[58] Field of Search ................... 260/45.7 P, 45.7 PT, 260/45.85 R, 941, 969; 521/106, 107; 560/8

[56] References Cited

U.S. PATENT DOCUMENTS

| | | | |
|---|---|---|---|
| 2,631,162 | 3/1953 | Ladd et al. | 260/946 |
| 2,877,260 | 3/1959 | Campbell et al. | 260/977 |
| 3,005,000 | 10/1961 | Cooper | 260/977 |
| 3,196,190 | 7/1965 | Nischk et al. | 260/941 |
| 3,779,956 | 12/1973 | Morehouse | 260/2.5 AJ |
| 3,781,388 | 12/1973 | Jenkner et al. | 260/953 |
| 3,801,542 | 4/1974 | Toy et al. | 260/45.85 R |

OTHER PUBLICATIONS

Komkov et al., "Chem. Abs.", 1959, 9036a.
Pudovik et al., "Reviews Uspekhi Khimii", vol. 37, pp. 317 and 323, May, 1968.
Kabachuk et al., "Chem. Abs.", vol. 42, (1948), 7241-7242.
Kosolapoff et al., "Organic Phosphorus Compounds", vol. 7, (1977), pp. 24 and 29.

*Primary Examiner*—Anton H. Sutto
*Attorney, Agent, or Firm*—Scott J. Meyer; James W. Williams, Jr.

[57] ABSTRACT

The present invention relates to 2-chloroethylphosphonate mixtures which are effective flame retardants for organic polymeric materials and have especially beneficial effects on rise and tack-free times in the production of rigid polyurethane foams.

1 Claim, No Drawings

2-CHLOROETHYL PHOSPHONATE COMPOSITIONS

CROSS-REFERENCE TO RELATED APPLICATION

This is a continuation-in-part of application Ser. No. 855,533, filed Nov. 28, 1977, which in turn is a continuation of application Ser. No. 831,707, filed Sept. 9, 1977 both now abandoned.

BACKGROUND OF THE INVENTION

The present invention relates to 2-chloroethyl phosphonate mixtures, a process for the preparation thereof and flame retardant compositions comprising organic polymers together with said 2-chloroethyl phosphonate mixtures.

Certain phosphorus esters such as phosphate esters have been employed heretofore as flame retardant additives but have suffered from the defect of low-molecular weight and loss by volatilization from the substrate polymeric materials in which the phosphates were employed. For example, the addition of such phosphates to a polyurethane foam resulted in loss of some of the phosphates when the foams were heat aged, with consequent reduction of fire-retardancy.

In other cases, the flame retardant additives do not lend themselves well to certain desired formulation characteristics in production of rigid polyurethane foams such as cream time, string time, rise time and tack-free time. Cream time is the time interval between (a) the start of the final mixing in laboratory or batch type mixing or the time the material is first poured in machine mixing and (b) the point at which the clear mixture turns creamy or cloudy and starts to expand. String time is the time between pouring the mixed liquids into the container and the time that long strings of tacky material can be pulled away from the surface of the foam when the surface is touched with a wooden spatula or with the fingers. Rise time is the time interval between the liquid mixture being poured into the mold and the completion of expansion of the foaming mass. Tack-free time is the time between pouring the liquid mixture and the time that the surface of the foam can be touched with a spatula or a finger without sticking. The aforesaid definitions are taken from "A Glossary of Urethane Industry Terms" by S. Alan Stewart, The Martin Sweets Company, Inc., 1971.

DESCRIPTION OF THE INVENTION

It has now been found that certain 2-chloroethyl phosphonate mixtures are effective flame retardants for organic polymeric materials. A particularly useful advantage of these phosphonate mixtures is a beneficial effect on rise and tack-free times in rigid polyurethane foam formulation. These mixtures are found to provide shorter rise and tack-free times than the purified major components of the mixtures.

According to another aspect of the invention, reduction of the acidities of the 2-chloroethyl phosphonate mixtures is provided by preparation of the mixtures in the presence of lower alkyl ($C_{1-4}$) acrylate esters. Reduction of acidities of these flame retardant additives facilitates the production of rigid polyurethane foams having improved foam characteristics.

The general method for the preparation of the 2-chloroethyl phosphonate products of this invention comprises step-wise treatment of phosphorus trichloride with ethylene oxide (step 1), followed by treatment with acrylic acid (step 2). The product is a mixture of several phosphonates; the two major components being 2-chloroethyl 3-[bis(2-chloroethoxy)phosphonyl]propionate

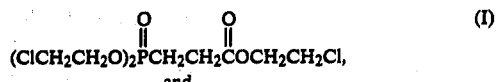

and
bis-(2-chloroethyl) 2-chloroethylphosphonate

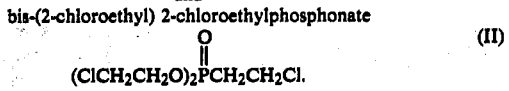

It is believed that other components of the mixture (minor components, not identified) may be the following:

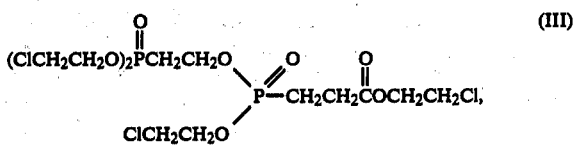

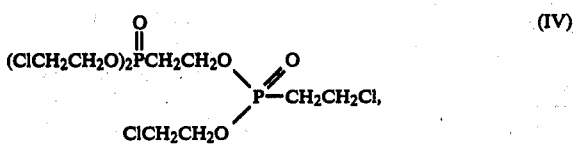

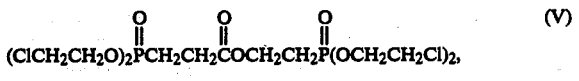

and

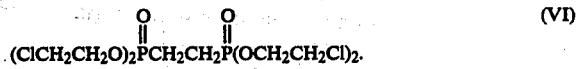

Structures II and IV are reported to be the major products of thermal isomerization of tris(2-chloroethyl) phosphite [see M.I. Kabacknik and P.A. Rossiikaia, *Bull. Acad. Sci. USSR,* ser. chem. 515 (1946); and Netherlands Patent Application No. 7,507,483 to Mobil Oil Corp.]

The amounts of the components of the mixture of the present invention vary according to the ratio of reactants used. For example, the amount of I is greatest when at least a molar equivalent of acrylic acid is used for each mole of phosphite intermediate. As the amount of acrylic acid used decreases below a molar equivalent, component I of the mixture decreases and II increases.

It will be appreciated that applicants are not bound by the aforesaid number and chemical structures of minor components in the mixtures, it being understood that the specific number and structures of these minor components are unknown and cannot presently be defined precisely or expressly described other than by the process by which they are made.

The temperature of the first step, the reaction of the phosphorus trichloride with the epoxide, may be in the range of about −20° C. to 125° C., the preferred range being 0° to 50° C.

Stoichiometric amounts of the phosphorus trichloride and epoxide, that is, enough epoxide to react with all of the chlorine bonded to phosphorus, are generally used in the first step, but the process can be carried out with an excess over the theoretical proportions of either reactant. The epoxide is usually added to stirred and cooled phosphorus trichloride, preferably in the presence of a catalyst, for example, hydrogen chloride or ethylene chlorohydrin.

Further refining of the phosphorus ester intermediate product of step 1 is unnecessary, and the addition of acrylic acid can usually be started in the same reaction vessel as soon as the temperature has been adjusted to the desired level for the second step. A stoichiometric amount of the acrylic acid is preferred, based upon the amount of trivalent phosphorus ester produced in step 1, but larger amounts, e.g. 1 to 20 mole% excess, or lesser amounts, e.g. as little as 40% of theory of acrylic acid, can be used.

The addition of acrylic acid to the intermediate phosphite ester of the first step, may be carried out at about 20° C. to 150° C., or preferably from about 30° C. to about 140° C. Additional warming, e.g. up to 185° for several hours, may be used to complete conversion of essentially all the phosphite to phosphonate structures.

Conduction of the second step in the presence of lower alkyl acrylate esters, for example, ethyl or methyl acrylate, has been found beneficial in reduction of the acidity of the phosphonate product mixture. About 1 to 20 mole percent of acrylate ester, based on the phosphite intermediate produced in step 1, is effective in reducing the acidity. Part or all of the acrylate ester can be added to the phosphite intermediate before the addition of acrylic acid is started. Or part of the acrylate, e.g. half, may be added before the addition of acrylic acid and the remainder after the addition of acrylic acid. Or the acrylate ester may be added simultaneously with the acrylic acid. The addition of all the acrylate ester after the acrylic acid addition is complete can reduce acidity, but this method may not be as effective as when at least part of the acrylate ester is present in the reaction mixture when the acrylic acid is being added.

Stripping at elevated temperatures and/or reduced pressures may be used to remove small amounts of side reaction products. Standard procedures can be used to further reduce acidity if needed, for example, washing with basic solutions or treatment with orthoformate esters or epoxides. For example, the product may be treated with aqueous sodium carbonate in order to neutralize any residual acidity. Another treatment which may be employed to carry the reaction to completion is an esterification treatment utilizing an esterifying agent such as triethyl orthoformate. Such after treatments, however, are not essential.

The following examples illustrate specific embodiments of the present invention, but are not limitative of the scope of the invention.

EXAMPLE 1

(a) Ethylene oxide (15.0 moles) is added sub-surface to a solution of 5.0 moles of phosphorus trichloride containing 6.0 g. of 2-chloroethanol with cooling at 15°–20° C. A solution of 269.5 g. of the resulting product [about 90% tris(2-chloroethyl) phosphite] and 0.05 mole of ethyl acrylate is warmed to 50°, and 0.85 mole of acrylic acid is added in 5.75 hr. with maintenance at 50°–55°. The reaction mixture is warmed at 50°–55° for 0.5 hr more, and a 50.5 g. portion (I) is removed. Ethyl acrylate (4.2 g.) is added to the remainder which is then warmed to 160° in 1.5 hr., kept at 160°–165° for 0.5 hr, and stripped to 150°/0.15 mm, giving 264.3 g. of yellow liquid having $^{31}P$ nmr signals at 30.4 ppm for 2-chloroethyl 3-[bis-(2-chloroethoxy)phosphinyl]propionate, at 26.2 ppm for bis(2-chloroethyl) 2-chloroethylphosphonate, and at 30.7, 27.5, and 26.9 ppm for other 2-chloroethyl phosphonates; acidity 0.79 meq/100 g.

(b) Similar treatment of portion (I), except that additional ethyl acrylate was not added, gave 48.4 g. of yellow liquid, acidity 1.40 meq/100 g.

EXAMPLE 2

A 269.5 g. portion of crude phosphite prepared from phosphorus trichloride and ethylene oxide as in Example 1 was stirred under $N_2$ and warmed to 50° C., and 0.85 mole of acrylic acid was added in 5 hr. with maintenance at 50°–55°. The reaction mixture was then warmed and stripped as in Example 1, giving a mixture of phosphonates having an acidity of 7.49 meq/100 g. (compared to 0.79 meq/100 g. for the ethyl acrylate treated product of Example 1). The addition of 0.05 mole of ethyl acrylate, followed by warming at 160°–165° for 0.75 hr., reduced the acidity to 4.93 meq./100 g. However, the acidity was not further reduced by similar treatment with an additional 0.05 mole of ethyl acrylate.

EXAMPLE 3

(a) Ethyl acrylate (0.05 mole) was added to 269.5 g. of crude phosphite prepared as in Example 1. This solution was stirred under nitrogen and warmed to 50°, and 0.50 mole of acrylic acid was added in 3 hr. with cooling at 50°–55°. The reaction mixture was kept at 50°–55° for 0.5 hr. more, and 0.05 mole of additional ethyl acrylate was added. The temperature was raised to 170° in 1.75 hr. and kept at 168°–172° for 3 hr. Stripping to 150° at 0.15 mm. gave 298.9 g. of yellow liquid having $^{31}P$ nmr signals at 30.4 ppm for 2-chloroethyl 3-[bis(2-chloroethoxy)phosphinyl]propionate, at 26.2 ppm for bis(2-chloroethyl) 2-chloroethylphosphonate, and at 30.8, 27.5, and 26.8 ppm for other 2-chloroethyl phosphonates; acidity 0.30 meq/100 g.

(b) Similar treatment of 269.5 g. of crude phosphite from phosphorus trichloride and ethylene oxide with 0.45 mole of acrylic acid, but without the use of acrylate esters to reduce acidity, gave a mixture of 2-chloroethyl phosphonates having an acidity of 5.0 meq/100 g.

EXAMPLE 4

Ethylene oxide, 816 g. (18.5 m) is added subsurface to a stirred solution of 824 g. (6.0 m) of phosphorus trichloride and 8.2 g. of 2-chloroethanol in 2.75 hr with cooling at 15°–20° C. The resulting reaction mixture consists of about 90% tris(2-chloroethyl) phosphite, the remainder being a mixture of phosphonates, is warmed to 80°, and 389 g. (5.4 m.) of acrylic acid containing 100 ppm of hydroquinone monomethyl ether is added in 1.2 hr with cooling at 80°–85°. The reaction mixture is warmed to 130° in 0.5 hr and kept at 130°–140° for 3.25 hr. Stripping to 165°/1 mm leaves 1881 g. of yellow liquid which is a mixture of 2-chloroethyl phosphonates, acidity 9.7 meq/100 g. Washing of a 622 g. portion with 5% sodium carbonate solution, followed by stripping at reduced pressure, gives 590 g. acidity 3.7 meq./100 g. Distillation of a portion of the washed material gives bis(2-chloroethyl) 2-chloroethylphosphonate, b.p. 148°–151°/0.5 mm., and 2-chloroethyl 3-[bis(2-chloroethoxy)phosphinyl]propionate, b.p. 189°–191°/0.1 mm, leaving a mixture containing higher molecular weight 2-chloroethyl phosphonates as undistilled residue.

EXAMPLE 5

Rigid polyurethane foam formulations were prepared utilizing the following components in parts by weight as stated:

| Components | Parts by Weight |
| --- | --- |
| Sucrose-based polyol | 100 |
| Hydroxyl no = 470 | |
| (Multranol 4034 | |
| Mobay Chemical Co.) | |
| Water, distilled | 1 |
| Trichloromonofluoro- | 35 |
| methane (Freon 11, | |
| DuPont) | |
| Amine catalyst, blend of | 3 |
| triethylenediamine (80%) and | |
| dimethylethanolamine (20%) | |
| (Dabco R-8020, Air Products) | |
| Surfactant - Silicone | 1.6 |
| (DC-193, Dow Corning) | |
| Polymethylene polyphenyl | 140 |
| isocyanate, NCO eq. wt. = 131 | |
| (Mondur MR, Mobay | |
| Chemical Co.) | |
| Fire retardant | |
| additive | 20 |
| Total | 300.6 |

The polyurethane foam formulations resulting from the heating together of the components set forth above utilizing five different fire retardant additives were tested for oxygen index, cream time, string time, tack-free time and rise time. The latter four times are defined above and are given in seconds. Oxygen index is defined as the minimum concentration of oxygen, expressed as volume percent, in a mixture of oxygen and nitrogen that will support combustion under standard test procedures in accordance with ASTM D2863-70.

The five different fire retardant additives were as follows:

| Formulation | Additive |
| --- | --- |
| A | None (control sample) |
| B | Antiblaze ® 78 |
| | (Mobil Chemical Co.- reported |
| | to be comprised of structures |
| | II and IV)* |
| C | Product of Example 3 (a) |
| D | Product of Example 1 (a) |
| E | Major pure component II* |
| | distilled from Antiblaze ® 78 |
| F | Major pure component I* |
| | distilled from product |
| | of Example 4 |

*Chemical structures shown above

The test results with the aforesaid six formulations A to F, inclusive, were as follows:

| | Formulation | | | | | |
| --- | --- | --- | --- | --- | --- | --- |
| Property | A | B | C | D | E | F |
| Cream time | 17 | 18 | 18 | 18 | 18 | 18 |

-continued

| | Formulation | | | | | |
| --- | --- | --- | --- | --- | --- | --- |
| Property | A | B | C | D | E | F |
| String time | 66 | 78 | 77 | 73 | 70 | 78 |
| Tack-free | | | | | | |
| time | 119 | 157 | 115 | 124 | 130 | 135 |
| Rise time | 140 | 168 | 158 | 160 | 165 | 165 |
| Oxygen index | 20.5 | 23.7 | 23.3 | 23.0 | 23.7 | 22.9 |

Evaluation of the above results indicates cream time, string time and oxygen index of the mixtures of the invention (illustrative by formulations C and D) to be comparable to that of the commercial product B and the major pure components of formulations E and F. A most surprising effect is seen with tack-free time and rise time. In the latter tests, the major pure components of formulations E and F were about the same. Mixtures C and D, however, show a significant decrease in rise and tack-free times (up to 11.5% decrease in tack-free time and 6% in rise time). The advantage of these decreases in times when using the mixtures of the invention is in the resulting increased production capacity. Thus, one can gain the advantages of a fire retardant foam with minimal increase in production times by use of the mixtures as distinguished from use of the separate major components. This advantageous decrease in rise and tack-free times without adverse effects upon the cream and string times in the first retardant mixtures is a surprising and unexpected result.

The 2-chloroethyl phosphonate mixtures of this invention can be incorporated in other polyurethane formulations having similar such fire retardant properties and advantages in rise and tack-free times. Essentially, these polyurethanes are condensation products of a diisocyanate and a compound having a molecular weight of at least about 500 and preferably about 1500-5000 and at least two reactive hydrogen ions (hydrogen donors). The useful active-hydrogen containing compounds can be polyesters prepared from polycarboxylic acids and polyhydric alcohols, polyhydric polyalkylene ethers having at least two hydroxy groups, polythioether glycols, polyesteramides and similar such materials.

Generally, use of from about 0.1 to about 20% by weight of the 2-chloroethyl phosphonate mixture will produce the desired flame retardancy and improvements in rise and tack-free times. These mixtures can be incorporated into the polyurethane formulation, for example, from solution or by direct addition to the organic polymer.

What is claimed is:

1. The composition prepared by the step-wise treatment of phosphorus trichloride with ethylene oxide in about stoichiometric proportions and at temperatures of from about −20° C. to about 125° C. followed by treatment of the resulting phosphite ester intermediate with from about 0.4 to about 1.2 moles of acrylic acid per mole of said phosphite ester intermediate in the presence of lower alkyl acrylate ester to substantially reduce the acidity of said composition and at temperatures of from about 20° C. to about 185° C. until substantially all the phosphite ester is converted to phosphonate structures.

* * * * *